(12) United States Patent
Beaty et al.

(10) Patent No.: US 6,645,368 B1
(45) Date of Patent: Nov. 11, 2003

(54) METER AND METHOD OF USING THE METER FOR DETERMINING THE CONCENTRATION OF A COMPONENT OF A FLUID

(75) Inventors: Terry Allen Beaty, Indianapolis, IN (US); Lance Scott Kuhn, Fishers, IN (US); Vladimir Svetnik, Carmel, IN (US); David W. Burke, Carmel, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/530,171
(22) PCT Filed: Dec. 21, 1998
(86) PCT No.: PCT/US98/27203
§ 371 (c)(1), (2), (4) Date: Apr. 24, 2000
(87) PCT Pub. No.: WO99/32881
PCT Pub. Date: Jul. 1, 1999

Related U.S. Application Data

(63) Continuation-in-part of application No. 08/996,280, filed on Dec. 22, 1997, now abandoned.

(51) Int. Cl.⁷ ..................... G01N 27/327; G01N 27/403
(52) U.S. Cl. .............. 205/792; 205/777.5; 204/403.01; 204/401; 422/82.01
(58) Field of Search ............. 204/401, 403, 204/403.01; 205/777.5, 792; 422/82.01, 82.02, 82.03

(56) References Cited

U.S. PATENT DOCUMENTS

| 4,686,479 A | 8/1987 | Young et al. | 205/781.5 |
|---|---|---|---|
| 5,140,176 A | 8/1992 | Okino | 327/217 |
| 5,438,271 A | 8/1995 | White et al. | 324/444 |
| 5,575,403 A | 11/1996 | Charlton et al. | 221/31 |
| 5,630,986 A | 5/1997 | Charlton et al. | 422/64 |
| 5,792,668 A | 8/1998 | Fuller et al. | 436/149 |

FOREIGN PATENT DOCUMENTS

| DE | 4011428 | 11/1990 | |
| EP | 0 445 826 B1 | 11/1995 | G05B/19/042 |
| EP | 0 732 590 A2 | 9/1996 | B01N/35/00 |
| JP | 3260739 | 11/1991 | G05B/19/04 |
| JP | 8-262026 | 10/1996 | G01N/35/00 |
| JP | 10-10130 | 1/1998 | G01J/3/02 |
| WO | WO 97/39341 | 10/1997 | |

*Primary Examiner*—T. Tung
*Assistant Examiner*—Alex Noguerola
(74) *Attorney, Agent, or Firm*—Barnes & Thornburg

(57) ABSTRACT

An apparatus and method for determining the concentration of a medically significant component of a biological fluid comprise providing a cell supporting a chemistry which reacts with the medically significant component. Placement of first and second terminals of the cell in contact with first and second terminals, respectively, of an instrument permits the instrument to assess the reaction. The instrument determines a first response of the cell to a first signal, and determines based upon the first response whether to proceed with the determination of the concentration of the medically significant component of the biological fluid. If the determination is to proceed, the instrument determines the type of sample that has been applied. If the sample is a sample of a particular type, the instrument determines a first correction value based upon the cell's response to the third signal and combines the correction value with the result of the reaction assessment to produce an indication of the concentration of the medically significant component in the sample.

46 Claims, 6 Drawing Sheets

METER AND METHOD OF USING THE METER FOR DETERMINING THE CONCENTRATION OF A COMPONENT OF A FLUID

CROSS-REFERENCES TO RELATED APPLICATIONS

This application is a U.S. national counterpart application of international application Ser. No. PCT/US98/27203 filed Dec. 21, 1998, which claims priority to, and is a continuation-in-part application of, U.S. utility application Ser. No. 08/996,280 filed Dec. 22, 1997 (now abandoned).

BACKGROUND OF THE INVENTION

This invention relates to methods and apparatus for improving the accuracy of measurements made with instruments of the type described in, for example, U.S. Patents: U.S. Pat. Nos. 5,243,516; 5,288,636; 5,352,351; 5,385,846; and 5,508,171. The invention is disclosed in the context of such an instrument, but is believed to be useful in other instruments of this general type as well.

There are a number of instruments for the determination of the concentrations of biologically significant components of bodily fluids, such as, for example, the glucose concentration of blood. There are, for example, the instruments described in U.S. Patents: U.S. Pat. Nos. 3,770,607; 3,838,033; 3,902,970; 3,925,183; 3,937,615; 4,005,002; 4,040,908; 4,086,631; 4,123,701; 4,127,448; 4,214,968; 4,217,196; 4,224,125; 4,225,410; 4,230,537; 4,260,680; 4,263,343; 4,265,250; 4,273,134; 4,301,412; 4,303,887; 4,366,033; 4,407,959; 4,413,628; 4,420,564; 4,431,004; 4,436,094; 4,440,175; 4,477,314; 4,477,575; 4,499,423; 4,517,291; 4,654,197; 4,671,288; 4,679,562; 4,682,602; 4,703,756; 4,711,245; 4,734,184; 4,750,496; 4,759,828; 4,789,804; 4,795,542; 4,805,624; 4,816,224; 4,820,399; 4,897,162; 4,897,173; 4,919,770; 4,927,516; 4,935,106; 4,938,860; 4,940,945; 4,970,145; 4,975,647; 4,999,582; 4,999,632; 5,108,564; 5,128,015; 5,243,516; 5,269,891; 5,288,636; 5,312,762; 5,352,351; 5,385,846; 5,395,504; 5,469,846; 5,508,171; 5,508,203; and 5,509,410: German Patent Specification 3,228,542: European Patent Specifications: 206,218; 230,472; 241,309; 255,291; and, 471,986: and, Japanese Published Patent Applications JP 63-128,252 and 63-111,453. There are also the methods and apparatus described in: Talbott, et al, "A New Microchemical Approach to Amperometric Analysis," Microchemical Journal, Vol. 37, pp. 5–12 (1988); Morris, et al, "An Electrochemical Capillary Fill Device for the Analysis of Glucose Incorporating Glucose Oxidase and Ruthenium (III) Hexamine as Mediator, Electroanalysis," Vol. 4, pp. 1–9 (1992); Cass, et al, "Ferrocene-Mediated Enzyme Electrode for Amperometric Determination of Glucose," Anal. Chem., Vol. 56, pp. 667–671 (1984); Zhao, "Contributions of Suspending Medium to Electrical Impedance of Blood," Biochimica et Biophysica Acta, Vol. 1201, pp. 179–185 (1994); Zhao, "Electrical Impedance and Haematocrit of Human Blood with Various Anticoagulants," Physiol. Meas., Vol. 14, pp. 299–307 (1993); Muller, et al., "Influence of Hematocrit and Platelet Count on Impedance and Reactivity of Whole Blood for Electrical Aggregometry,"Journal of Pharmacological and Toxicological Methods, Vol. 34, pp. 17–22 (1995); Preidel, et al, " In Vitro Measurements with Electrocatalytic Glucose Sensor in Blood," Biomed. Biochim. Acta, Vol. 48, pp. 897–903 (1989); Preidel, et al, "Glucose Measurements by Electrocatalytic Sensor in the Extracorporeal Blood Circulation of a Sheep," Sensors and Actuators B, Vol. 2, pp.257–263 (1990); Saeger, et al, "Influence of Urea on the Glucose Measurement by Electrocatalytic Sensor in the Extracorporeal Blood Circulation of a Sheep," Biomed. Biochim. Acta, Vol. 50, pp. 885–891 (1991); Kasapbasioglu, et al, "An Impedance Based Ultra-Thin Platinum Island Film Glucose Sensor," Sensors and Actuators B, Vol. 13–14, pp. 749–751 (1993); Beyer, et al, "Development and Application of a New Enzyme Sensor Type Based on the EIS-Capacitance Structure for Bioprocess Control," Biosensors & Bioelectronics, Vol. 9, pp. 17–21 (1994); Mohri, et al, "Characteristic Response of Electrochemical Nonlinearity to Taste Compounds with a Gold Electrode Modified with 4-Aminobenzenethiol," Bull. Chem. Soc. Jpn., Vol. 66, pp. 1328–1332 (1993); Cardosi, et al, "The Realization of Electron Transfer from Biological Molecules to Electrodes," *Biosensors Fundamentals and Applications,* chapt. 15 (Turner, et al, eds., Oxford University Press, 1987); Mell, et al, "Amperometric Response Enhancement of the Immobilized Glucose Oxidase Enzyme Electrode," Analytical Chemistry, Vol. 48, pp. 1597–1601 (Sept. 1976); Mell, et al, "A Model for the Amperometric Enzyme Electrode Obtained Through Digital Simulation and Applied to the Immobilized Glucose Oxidase System," Analytical Chemistry, Vol. 47, pp. 299–307 (Feb. 1975); Myland, et al, "Membrane-Covered Oxygen Sensors: An Exact Treatment of the Switch-on Transient," Journal of the Electrochemical Society, Vol. 131, pp. 1815–1823 (Aug. 1984); Bradley, et al, "Kinetic Analysis of Enzyme Electrode Response," Anal. Chem., Vol. 56, pp. 664–667 (1984); Koichi,"Measurements of Current-Potential Curves, 6, Cottrell Equation and its Analogs. What Can We Know from Chronoamperometry?" Denki Kagaku oyobi Kogyo Butsuri Kagaku, Vol. 54, no.6, pp. 471–5 (1986); Williams, et al, "Electrochemical-Enzymatic Analysis of Blood Glucose and Lactate," Analytical Chemistry, Vol. 42, no. 1, pp. 118–121 (Jan. 1970); and, Gebhardt, et al, "Electrocatalytic Glucose Sensor," Siemens Forsch.-u. Entwickl.-Ber. Bd., Vol. 12, pp.91–95 (1983). This listing is not intended as a representation that a complete search of all relevant prior art has been conducted, or that no better references than those listed exist. Nor should any such representation be inferred.

DISCLOSURE OF THE INVENTION

According to one aspect of the invention, an apparatus for determining the concentration of a medically significant component of a biological fluid comprises a cell for receiving a sample of the fluid. The cell supports a chemistry which reacts with the medically significant component and first and second terminals across which the reaction of the chemistry with the medically significant component can be assessed. The apparatus further comprises an instrument having first and second terminals complementary to the first and second terminals, respectively, of the cell. Placement of the first and second terminals of the cell in contact with the first and second terminals, respectively, of the instrument permits the instrument to assess the reaction. The instrument includes an assessment controller for applying across the first and second terminals of the instrument a first signal, determining a first response of the cell to the first signal, and determining based upon the first response whether to proceed with the determination of the concentration of the medically significant component of the biological fluid.

According to another aspect of the invention, an apparatus for determining the concentration of a medically significant component of a biological fluid comprises a cell for receiving a sample of the fluid. The cell supports a chemistry which reacts with the medically significant component and first and second terminals across which the reaction of the chemistry with the medically significant component can be assessed. The apparatus further comprises an instrument having first and second terminals complementary to the first and second terminals, respectively, of the cell. Placement of the first and second terminals of the cell in contact with the first and second terminals, respectively, of the instrument permits the instrument to assess the reaction. The instrument includes an assessment controller for applying across the first and second terminals of the instrument a first signal, determining a first correction value in response of the cell to the first signal, assessing the reaction of the medically significant component with the chemistry and combining the correction value with the result of the reaction assessment to produce an indication of the concentration of the medically significant component in the sample.

According to another aspect of the invention, an apparatus for determining the concentration of a medically significant component of a biological fluid comprises a cell for receiving a sample of the fluid. The cell supports a chemistry which reacts with the medically significant component and first and second terminals across which the reaction of the chemistry with the medically significant component can be assessed. The apparatus further comprises an instrument having first and second terminals complementary to the first and second terminals, respectively, of the cell. Placement of the first and second terminals of the cell in contact with the first and second terminals, respectively, of the instrument permits the instrument to assess the reaction. The instrument includes an assessment controller for applying across the first and second terminals of the instrument a first signal, determining the identity of the sample in response of the cell to the first signal, and producing an indication of the identity of the sample.

According to yet another aspect of the invention, a method for determining the concentration of a medically significant component of a biological fluid comprises providing a cell for receiving a sample of the fluid, and providing on the cell a chemistry which reacts with the medically significant component and first and second terminals across which the reaction of the chemistry with the medically significant component can be assessed. The method further comprises providing an instrument having first and second terminals complementary to the first and second terminals, respectively, of the cell. Placement of the first and second terminals of the cell in contact with the first and second terminals, respectively, of the instrument permits the instrument to assess the reaction. The method further comprises providing in the instrument an assessment controller, causing the assessment controller to apply across the first and second terminals of the instrument a first signal, causing the assessment controller to determine a first response of the cell to the first signal, and causing the assessment controller to determine, based upon the first response, whether to proceed with the determination of the concentration of the medically significant component of the biological fluid.

According to a further aspect of the invention, a method for determining the concentration of a medically significant component of a biological fluid comprises providing a cell for receiving a sample of the fluid, and providing on the cell a chemistry which reacts with the medically significant component and first and second terminals across which the reaction of the chemistry with the medically significant component can be assessed. The method further comprises providing an instrument having first and second terminals complementary to the first and second terminals, respectively, of the cell. Placement of the first and second terminals of the cell in contact with the first and second terminals, respectively, of the instrument permits the instrument to assess the reaction. The method further comprises providing in the instrument an assessment controller, causing the assessment controller to apply across the first and second terminals of the instrument a first signal, to determine a first correction value in response to the first signal, to assess the reaction of the medically significant component with the chemistry, and to combine the correction value with the result of the reaction assessment to produce an indication of the concentration of the medically significant component in the sample.

According to a further aspect of the invention, a method for determining the concentration of a medically significant component of a biological fluid comprises providing a cell for receiving a sample of the fluid, and providing on the cell a chemistry which reacts with the medically significant component and first and second terminals across which the reaction of the chemistry with the medically significant component can be assessed. The method further comprises providing an instrument having first and second terminals complementary to the first and second terminals, respectively, of the cell. Placement of the first and second terminals of the cell in contact with the first and second terminals, respectively, of the instrument permits the instrument to assess the reaction. The method further comprises providing in the instrument an assessment controller for applying across the first and second terminals of the instrument a first signal, determining the identity of the sample in response of the cell to the first signal, and producing an indication of the identity of the sample.

Illustratively, the first signal comprises a signal having an AC component. Further illustratively, the first signal comprises an AC signal.

Additionally illustratively, the method of, and apparatus for, determining the correction value, the method of, and apparatus for, determining the identity of the sample, and the method of, and apparatus for, determining whether to proceed with the determination of the concentration of the medically significant component of the biological fluid comprise the step of, and apparatus for, determining the impedance across terminals of the cell.

BRIEF DESCRIPTION OF THE DRAWINGS

The invention may best be understood by referring to the following detailed description and accompanying drawings which illustrate the invention. In the drawings:

FIG. 6 illustrates glucose concentration results achieved in several ten second glucose concentration determinations with standard glucose test solutions; and, FIG. 7 illustrates glucose concentration results achieved in several ten second glucose concentration determinations with standard glucose test solutions.

DETAILED DESCRIPTION OF ILLUSTRATIVE EMBODIMENTS

Figure 1:
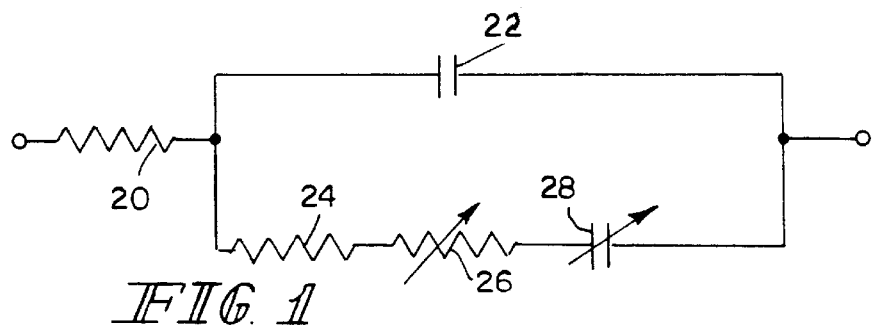
FIG. 1 illustrates a schematic diagram of a circuit useful in understanding the invention.

Instruments are known which employ devices such as disposable mediated amperometric cells (sometimes referred to hereinafter as biosensors) which provide, for example, characteristic electrical impedances when treated with biological fluids, blood or urine for example, having certain corresponding concentrations of biologically significant components, such as, for example, glucose. Such measurement systems are known to be susceptible to variations in the temperature of the biological fluids and to interference by the presence in the biological fluids of other components, known and sometimes referred to hereinafter as interferrents. In many cases, these sources of error have effects on the biosensor output of the same order of magnitude as the concentration of the component, measurement of which is sought. It may not be possible to develop a biosensor which will measure only the concentration of the component whose concentration is sought in the presence of these sources of error. An example of this phenomenon is the hematocrit interference in a biosensor of the type described in U.S. Patents: U.S. Pat. Nos. 5,243,516; 5,288,636; 5,352,351; 5,385,846 and, 5,508,171, with the determination of the glucose concentration of whole blood. Since all whole blood contains red blood cells, and since the hematocrit can vary over a fairly wide range in individuals who might wish to rely upon such biosensor testing, the utility of a hematocrit-compensated glucose biosensor is clear.

Equally problematic is the sensitivity of many commercially available biosensors to the volume of the dopant biological fluid. In the case of glucose concentration of whole blood, for example, many presently available biosensors are sensitive to the volume of blood with which they are doped for determination of glucose concentration. Since many of the tests which are presently being conducted using biosensors are being conducted by people who are monitoring, for example, the glucose concentrations of their own blood, the volumes of the blood samples with which the biosensors are doped are not predictable with a great degree of certainty. While the careful design of the biosensor itself can prevent some errors, such as undoped biosensors, substantially underdoped biosensors and substantially overdoped biosensors, for example, it cannot practically take into account the full range of doping volume variation.

We have discovered that measurement of the real component or the imaginary component, or both, of the AC impedance of an appropriately designed biosensor provides reasonable insight into sample temperature and the concentrations of certain physical and chemical interferrents. In biosensors of the general types described in U.S. Patents: U.S. Pat. Nos. 5,243,516; 5,288,636; 5,352,351; 5,385,846; 5,508,171; 5,437,999; and, U.S. Ser. No. 08/985,840, filed Dec. 5, 1997 and assigned to the same assignee as this application, such physical interferrents include, for example, hematocrit, and such chemical interferrents include, for example, bilirubin, uric acid and oxygen. We have discovered that measurement of the real component or the imaginary component, or both, of the AC impedance of an appropriately designed biosensor also provides reasonable insight into the volume of a sample with which the biosensor is doped, and the identity of that sample; that is, whether the sample is a sample of blood or some other bodily fluid, or a sample of some control used, for example, in calibration or troubleshooting of the instrument. We have discovered that sample temperature, the concentrations of such physical and chemical interferrents, the identity of the sample and the sample volume can be ascertained at judiciously selected AC frequencies, providing reasonable isolation of the determinations of the effects of sample temperature, interferrent concentrations and sample volume and identity from each other, and thereby increasing the accuracy of, for example, the interferrent effect determinations, and their subsequent correction out of the indicated glucose concentration. We have also found that the speeds at which acceptably accurate readings of corrected glucose concentration are obtained can be markedly reduced. The appropriately designed biosensor must be able to tolerate the determination of these AC impedances, using, for example, AC signals having peak amplitudes in the range of a few tens of millivolts, without jeopardizing the measurement of the glucose concentration, which the biosensor will perform either before, concurrently with, or after it performs the AC impedance determination.

By way of example only, we have determined that in biosensors of the type described in U.S. Patents: U.S. Pat. Nos. 5,243,516; 5,288,636; 5,352,351; 5,385,846; 5,508, 171; 5,437,999; and, U.S. Ser. No. 08/985,840, it is possible to employ a low-magnitude, for example, less than about 40 mV rms or so, AC signal in the range of less than about 0.1 Hz to 10 KHz or so with no DC offset to compensate for sample temperature, hematocrit, bilirubin concentration, uric acid concentration and oxygen concentration, and to determine identity of the sample with which the biosensor is dosed, and adequacy of dosed blood sample volume for a test for glucose concentration. We have determined, for example, that at about 1300 Hz, both hematocrit and glucose concentration have relatively little effect on AC impedance, while sample volume and sample identity have relatively substantially greater, fairly readily ascertainable, effects on AC impedance. This provides an ideal way to determine the adequacy of the sample volume with which the biosensor is dosed and the identity of the sample. If the sample is determined to be blood, and the sample volume is determined to be inadequate to test meaningfully for hematocrit, glucose concentration, and so on, the test is discontinued and the user is notified of the discontinuance of the test.

We have determined that the combined effect of sample temperature and hematocrit can fairly effectively be isolated from other physical and chemical interferrents of interest using frequencies in the range of from about 2 KHz to about 10 KHz. So, for example, once the adequacy of the sample volume for test has been established, a 2 KHz signal can be applied to the biosensor and the real and imaginary components of impedance of the biosensor/sample system can be determined. This indicated impedance can be adjusted by an experimentally determined scaling factor governed by, among other things, the characteristics of the biosensor and the instrument, and combined with an indicated glucose concentration to arrive at a glucose concentration compensated for the combined effects of sample temperature and hematocrit.

These determinations illustratively are made before the amperometric determination of the glucose concentration of the blood sample. DC offset may be avoided, if necessary, to reduce the likelihood of affecting the amperometric determination of the glucose concentration which, it must be remembered, is going to be conducted subsequently in the illustrated embodiments. Similar procedures can be conducted, again in the illustrated embodiments before the amperometric determination of the glucose concentration, to determine the concentrations of other interferrents with chemistry for the glucose concentration determination, such as bilirubin, uric acid and oxygen. These determinations are conducted at frequencies at which their effects upon each other and upon other physical and chemical interferrents will be optimally decoupled from each other. For example, if, in the chemistry system of the amperometric cell, bilirubin and uric acid are chemical interferrents with each other, a frequency or range of frequencies should be selected for the bilirubin concentration determination, which frequency or range of frequencies is optimally unaffected by the concentrations of uric acid and any other physical and chemical interferrents in the sample. Similarly, a frequency must be selected for the uric acid concentration determination which is optimally unaffected by the concentrations of bilirubin and any other physical and chemical interferrents in the sample. In each case, however, the determined impedance is converted either directly or via a concentration determination which can also be displayed to the user or stored in the instrument for future reference, to a correction factor for application to the indicated glucose concentration in order to arrive at a more accurate glucose concentration determination.

The methods and apparatus are believed best understood by consideration of the equivalent circuit of an amperometric sensor of the type described in U.S. Patents: U.S. Pat. Nos. 5,243,516; 5,288,636; 5,352,351; 5,385,846; 5,508,171; 5,437,999; and, U.S. Ser. No. 08/985,840. That equivalent circuit is illustrated in FIG. 1. In FIG. 1, a resistor 20 represents the uncompensated resistance of the amperometric cell, a capacitor 22 represents the capacitance attributable to the double layer of charge on the dosed cell with potential applied, a resistor 24 represents the charge transfer resistance of the cell's chemistry, and a resistor 26 and a capacitor 28 represent the so-called Warburg impedance. While the lumped electrical parameter models of other types of amperometric sensors may differ from the model illustrated in FIG. 1, similar analyses of those models will yield conclusions similar to those reached here, namely, that the real and imaginary components of the cells' or biosensors' electrical impedances provide techniques for determining quantitatively with some reasonable degree of accuracy the effects of interferrent concentrations, sample volume and sample identity on the concentration of a biologically significant component of a sample of a body fluid. These conclusions give the instrument and cell designer useful techniques for determining the adequacy of the volume of a sample applied to a biosensor, for determining the identity of the sample, and for correcting the indicated concentration of a biologically significant component of the sample for the concentration(s) of such interferrent(s) so that the effects of the concentration(s) of such interferrent(s) can be reduced in the indicated concentration of the biologically significant component of interest to provide more accurate information on the concentration of the biologically significant component of interest.

Blood sample studies analyzing the magnitudes of the real and imaginary components of the impedance of the equivalent circuit of FIG. 1 have established that in the range of about 1 KHz–10 KHz, there is very little dependence of the imaginary component of impedance on glucose concentration of the sample, while there is sufficient dependence of the magnitude of impedance on the combination of sample temperature and hematocrit to permit a sample first to be subjected to a low-magnitude AC signal in this frequency range, the magnitude of impedance to be determined, and a combined sample temperature/hematocrit correction factor to be combined with the indicated glucose concentration determined using the amperometry techniques described in, for example, U.S. Patents: U.S. Pat. Nos. 5,243,516; 5,288, 636; 5,352,351; 5,385,846; 5,508,171; 5,437,999; and, U.S. Ser. No. 08/985,840, to yield a glucose concentration corrected for the combined effects of sample temperature and hematocrit. Similar techniques can be employed to determine sample volume and sample type. The sample volume determination, however, ordinarily will result in a go-no go determination for the remainder of the assay. The sample type determination ordinarily will determine whether the instrument proceeds to a glucose concentration subroutine including, for example, determination of interferrent correction factors, or to a diagnostic subroutine used to set up the instrument for a later glucose concentration determination.

Figure 2:
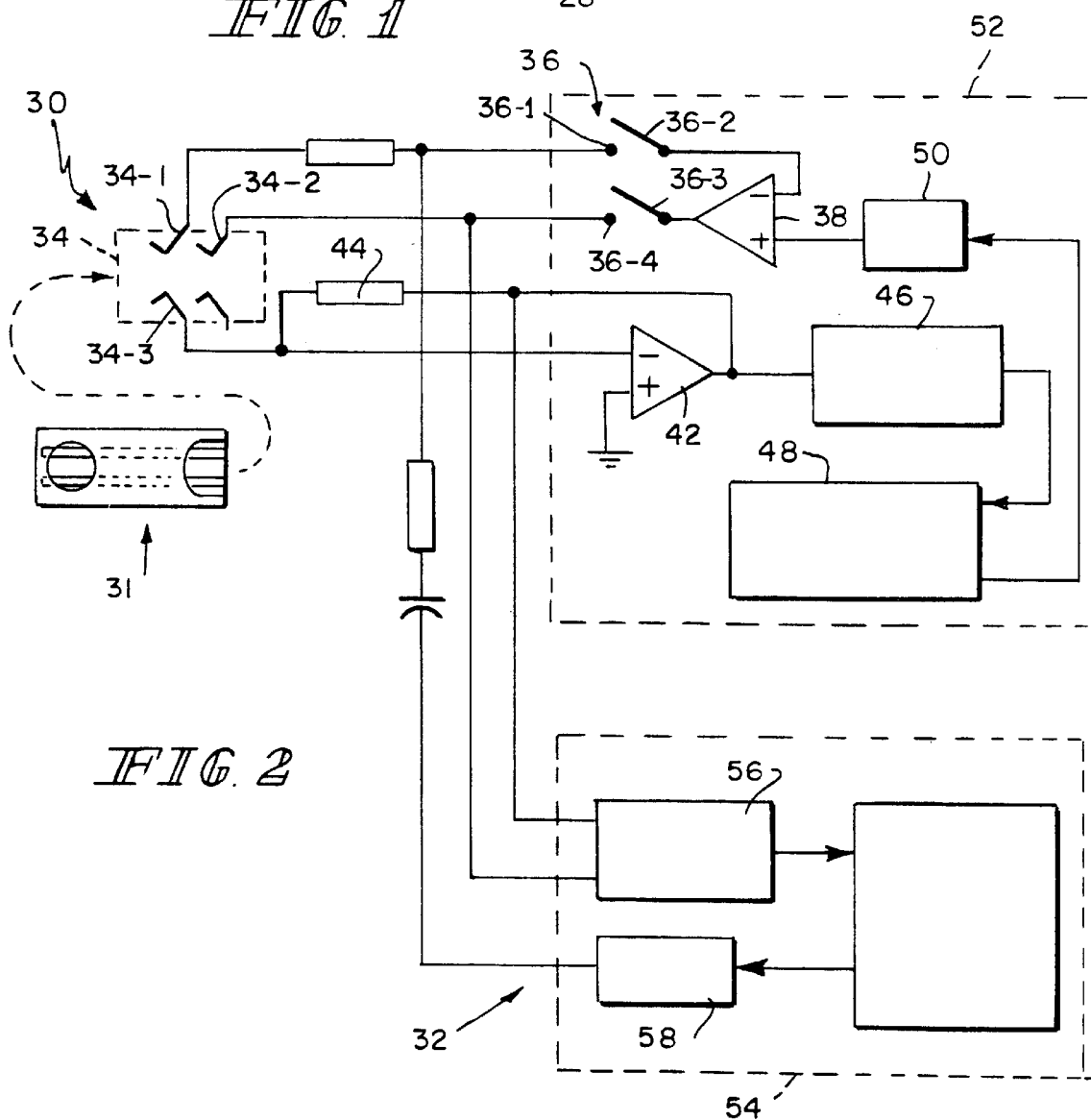
FIG. 2 illustrates a partly block and partly schematic diagram of an instrument constructed according to the present invention.

Referring to FIG. 2, a strip connector 30 of the general type illustrated in U.S. Patents: U.S. Pat. Nos. 5,243,516; 5,288,636; 5,352,351; 5,385,846; and, 5,508,171; makes contact between a disposable amperometric sensor cell or biosensor 31 of the general type illustrated in those patents and the instrument 32. The indicated glucose concentration functionality of the instrument 32 is largely as described in those patents. However, additional functions, namely, the correction of the indicated glucose concentration for blood sample volume and the combined effect of sample temperature and hematocrit of the blood sample under test, are implemented in the instrument 32 according to the present invention. It has been established that eight bit analog-to-digital (A/D) and digital-to-analog (D/A) computational power permits the instrument 32 to achieve accuracies in the range of about one-half percent or less. A first terminal 34-1 of a connector 34 is coupled through a 10 KΩ resistor to a terminal 36-1 of a switch 36. A terminal 36-2 of switch 36 is coupled to the inverting, or–, input terminal of a difference amplifier 38. An output terminal of amplifier 38 is coupled to a terminal 36-3 of switch 36. A terminal 36-4 of switch 36 is coupled to a terminal 34-2 of connector 34. DC excitation across the biosensor 31 is established by the output of amplifier 38. For accurate setting of DC excitation of the biosensor 31, feedback from terminal 34-1 is returned to the– input terminal of amplifier 38. Terminals 34-1 and 34-2 contact a common electrode on biosensor 31 for enhanced accuracy of excitation.

A terminal 34-3 of connector 34 is coupled to a– input terminal of a difference amplifier 42. An output terminal of amplifier 42 is coupled through a 7.5 KΩ resistor 44 to the– input terminal thereof The non-inverting, or+, input terminal of amplifier 42 is coupled to the common of the circuit power supply. An output terminal of amplifier 42 is coupled to an input terminal of a thirteen bit A/D converter 46. An output port of A/D converter 46 is coupled to an input port of a processor 48 with supporting functions which performs the indicated glucose measurement functions as described in U.S. Patents: U.S. Pat. Nos. 5,243,516; 5,288,636; 5,352, 351; 5,385,846; and, 5,508,171. An output port of processor 48 is coupled to an input port of an eight bit D/A converter 50. An output terminal of D/A converter 50 is coupled to the+ input terminal of amplifier 38. The functions of components 38, 42, 46, 48 and 50 illustratively, although not by any means necessarily, are embodied in an application-specific integrated circuit(ASIC) 52. The remaining, hematocrit compensating and sample volume determining functions of instrument 32 illustratively are embodied in a NEC μPD78054 microprocessor(μP) 54 which also has input A/D and output D/A converting capabilities 56 and 58, respectively. In FIG. 2, the input A/D and output D/A capabilities 56, 58 are illustrated separately from the processing functions of μP 54 for purposes of clarity. Terminal 36-4 of switch 36 is coupled to an input terminal of A/D converter 56. The output terminal of amplifier 42 is coupled to an input terminal of A/D converter 56. The output terminal of D/A converter 58 is coupled through a 0.1 µF capacitor and a 400 KΩ resistor in series to terminal 36-1 of switch 36 for AC excitation in this example. Here, an AC excitation signal is summed with the DC excitation provided by amplifier 38.

The calculations of the real and imaginary components of the AC impedance of the biosensor cell 31 coupled to terminals 34-1, -2 and -3 are made by exciting terminal 34-2 of connector 34 at the desired frequency, for example, 1300 Hz or 10 KHz, at which the parameter to be determined, be it sample identity or volume or hematocrit, or whatever other parameter is of interest and can be determined this way, varies with sufficient magnitude and phase and is optimally uncoupled from, that is, is not interfered with by, the concentrations of other components of the blood on the cell 31.

The calculation of the real and imaginary components of the cell 31 impedance from the AC excitation and response are achieved as follows. The eight bit excitation samples are N values E(0), E(1), E(2), . . . E(N−1). These values are developed by sampling the excitation by A/D converter 56. The eight bit response samples are N values V(0), V(1), V(2), . . . V(N−1). These values are A/D converted by A/D converter 56 and returned to the processor function of µP 54. Terminal 34-2 of connector 34 provides the common terminal against which these values are referenced. A scale factor K accounts for various gain factors involved in excitation and measurement. The excitation frequency is F Hz. The sample rate is MF, where M illustratively has a value of 5 or more. The period between samples is thus 1/MF sec. Arrays S(n) and C(n) of sine and cosine values are calculated and stored in program memory in µP 54 according to the following relations:

$$S(n)=\sin(2\pi F(n/MF)), n=0 \text{ to } (N-1)$$

$$C(n)=\cos(2\pi F(n/MF)), n=0 \text{ to } (N-1).$$

The real and imaginary components of excitation are calculated as follows:

$$Ere = \sum_{n=0}^{N-1} S(n)E(n)$$

The real and imaginary components of response are calculated as $$Eim = \sum_{n=0}^{N-1} C(n)E(n)$$

follows:

$$Vre = \sum_{n=0}^{N-1} S(n)V(n)$$

$$Vim = \sum_{n=0}^{N-1} C(n)V(n)$$

The magnitudes of the excitation and response are calculated as follows:

$$E=(Ere^2+Eim^2)^{1/2},$$

$$V=(Vre^2+Vim^2)^{1/2}.$$

The magnitude of the strip impedance can then be calculated:

$$|Z|=KE/V.$$

The phase of the strip impedance can also be calculated:

$$\arctan\left(\frac{Vim}{Vre}\right) - \arctan\left(\frac{Eim}{Ere}\right) = \angle Z$$

Thus, a measurement of actual glucose concentration using an instrument 32 of the type illustrated in FIG. 2 proceeds as follows. A sample of blood is applied to the biosensor 31. Immediately after the instrument 32's electronics detect the deposit of the droplet on the biosensor 31, an AC signal having a frequency of, for example, 1300 Hz is applied across terminals 34-2–34-3 of connector 34 and the resulting current is indirectly sampled by µP 54 by measuring the excitation and response voltages and using the scale factor to obtain current. The impedance magnitude and phase angle are calculated. Using these values, a look-up table in the µP 54's program memory is consulted to ascertain the nature of the sample and, if blood, whether there is sufficient volume in the blood sample to proceed with the glucose determination phase of the assay. If not, the assay is terminated and this outcome is displayed on the instrument 32's display. If there is sufficient volume to continue with the glucose determination, an AC signal at another frequency, for example, 10 KHz, is applied across terminals 34-2–34-3 of connector 34 and the resulting current is sampled by µP 54. The impedance and phase angle are again calculated at this second frequency. A second look-up table in the µP 54's program memory is consulted for an indicated glucose-to-actual glucose correction factor. This correction factor may be a constant, for example, zero, for indicated glucose concentrations less than a first indicated glucose concentration, and variable for indicated glucose concentrations greater than that first indicated glucose concentration, for example. In any event, that correction is stored, and the determination of the indicated glucose concentration proceeds generally as described in U.S. Patents: U.S. Pat. Nos. 5,243,516; 5,288,636; 5,352,351; 5,385,846; and 5,508,171, for example. Once the indicated glucose concentration has been obtained, the correction is then retrieved and applied to the indicated glucose concentration to arrive at the actual glucose concentration which is displayed on the instrument 32's display and/or stored in the instrument 32's memory.

Figure 3:
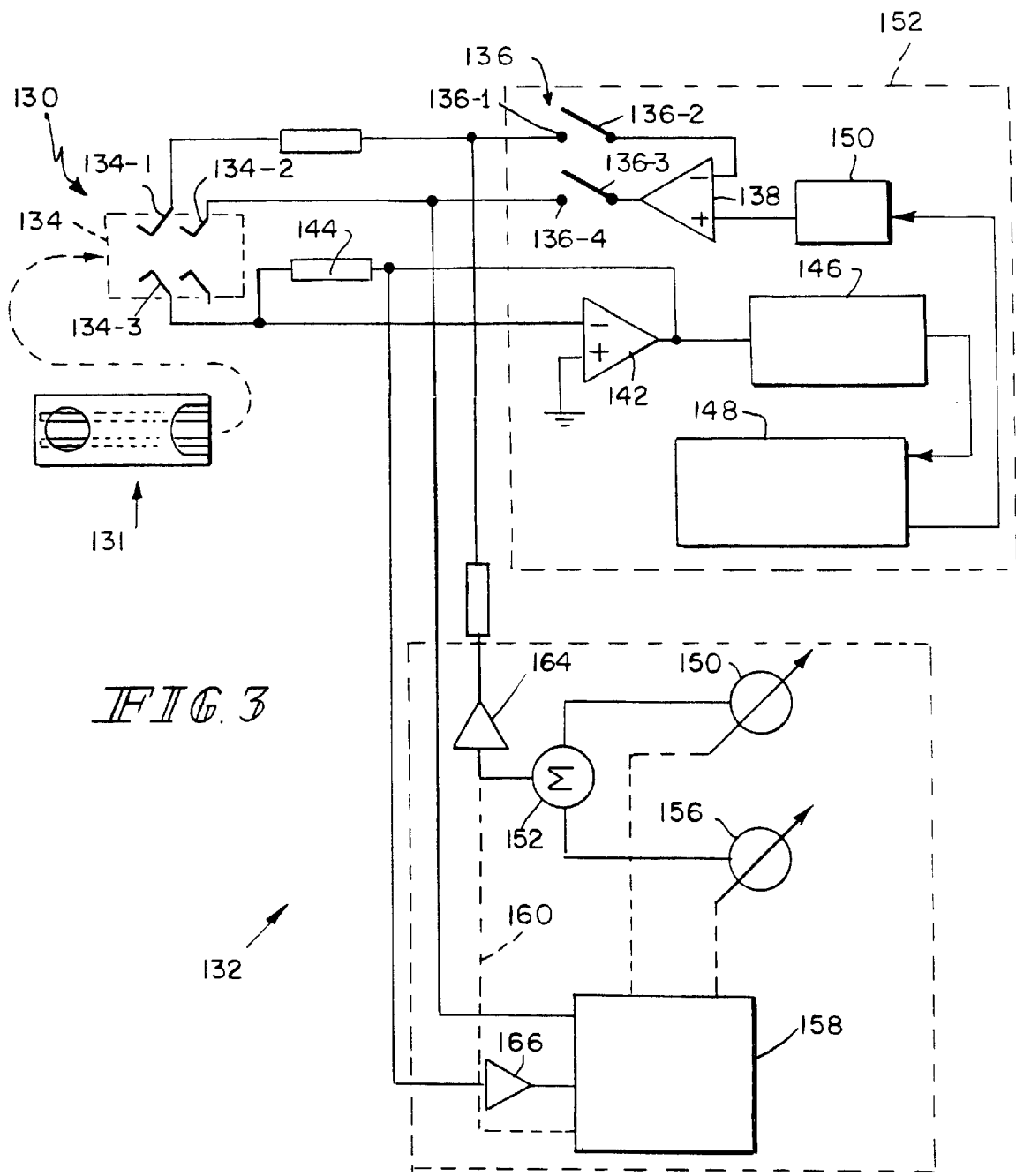
FIG. 3 illustrates a partly block and partly schematic diagram of another instrument constructed according to the present invention.

Another embodiment of the invention is illustrated in partly block and partly schematic form in FIG. 3. There, an instrument 132 includes a strip connector 130 of the same general type as strip connector 30 illustrated in FIG. 2. Strip connector 130 is designed to make contact to a biosensor 31. A first terminal 134-1 of a connector 134 is coupled through a 10 KΩ resistor to a terminal 136-1 of a switch 136. A terminal 136-2 of switch 136 is coupled to the− input terminal of a difference amplifier 138. An output terminal of amplifier 138 is coupled to a terminal 136-3 of switch 136. A terminal 136-4 of switch 136 is coupled to a terminal 134-2 of connector 134. DC excitation across the biosensor 31 is established by the output of amplifier 138. For accurate setting of DC excitation of the biosensor 31, feedback from terminal 134-1 is returned to the− input terminal of amplifier 138. Terminals 134-1 and 134-2 contact a common electrode on biosensor 31 for enhanced accuracy of excitation. A terminal 134-3 of connector 134 is coupled to a− input terminal of a difference amplifier 142. An output terminal of amplifier 142 is coupled through a 7.5 KΩ resistor 144 to the−input terminal thereof. The+input terminal of amplifier 142 is coupled to the common of the circuit power supply. An output terminal of amplifier 142 is coupled to an input terminal of a thirteen bit A/D converter 146. An output port of A/D converter 146 is coupled to an input port of a processor 148 with supporting functions which performs the indicated glucose measurement functions as described in U.S. Patents: U.S. Pat. Nos. 5,243,516; 5,288,636; 5,352,351; 5,385,846; and, 5,508,171. An output port of processor 148 is coupled to an input port of an eight bit D/A converter 150. An output terminal of D/A converter 150 is coupled to the+ input terminal of amplifier 138. The functions of components 138, 142, 146, 148 and 150 illustratively, although not by any means necessarily, are embodied in an ASIC 152.

The real and imaginary components of the AC impedance of the biosensor cell 31 coupled to terminals 134-1, -2 and -3 are calculated by excitation applied between terminals 134-2 and 134-3 of connector 134 at the desired frequencies, for example, by sweeping the low-magnitude AC voltage source 150 through a suitable frequency range of, for example, 0.1 Hz–100 Hz or 10 Hz–10 KHz, throughout some portion or all of which the parameter to be determined, be it sample identity, sample volume, sample temperature/hematocrit, oxygen concentration in the sample, or whatever other parameter is of interest and can be determined this way, varies with sufficient magnitude and phase and is optimally uncoupled from, that is, independent from, the concentrations of other components of the sample on the cell 31.

In the embodiment illustrated in FIG. 3, this low magnitude AC voltage excitation is summed at a summing junction 152 with an optional DC offset 156 which may be utilized if it aids the determination of the concentration of the interferent of interest. In the illustrated embodiment, the AC voltage and DC offset are both generated under the control of a microprocessor ($\mu$P) 158 which may be the same $\mu$P which manages the above-mentioned meter 132 functions, or may be a separate $\mu$P. The $\mu$P 158 will typically be programmed to sweep the AC voltage source 150 and adjust the DC offset, depending upon which interferent's concentration the $\mu$P 158 is determining. In this manner, each interferent's concentration may readily be ascertained in the optimum frequency range and at the optimum DC offset for isolation of that particular interferent's concentration. If $\mu$P 158 is used to control sweep and offset, a separate external connection 160 need not be provided from the summing junction 152 to the $\mu$P 158. Since $\mu$P 158 is going to determine the frequency response of the cell 31, the frequencies associated with the determined frequency response can be stored in the $\mu$P 158's memory as the frequency response is being determined. If some other mechanism is employed in the determination of the frequency response, however, it may be necessary to provide feedback 160 to the $\mu$P 158 of the output frequency of source 150, as well as the level of the DC offset 156. In any event, isolation of the summing junction 152 and any feedback path 160 from the cell 31 is provided by an operational amplifier 164 whose input is coupled to summing junction 152, and whose output is coupled through a suitably valued resistor into the feedback path of amplifier 138 to drive the cell 31. Similarly, isolation of the cell 31 from the frequency response-determining input of $\mu$P 158 is provided by an operational amplifier 166 coupled to the output of amplifier 142. Determination of the frequency response of the cell 31 proceeds in known fashion, for example, by fast Fourier transform (FFT) or other known $\mu$P 158-implemented frequency response determining mechanism. The frequency response characteristic of the cell 31 is then compared to the stored frequency response characteristic for the specific interferent whose concentration is being determined, an interferent concentration is determined, and an associated correction value for the indicated glucose concentration is determined and either stored for later use in correcting the indicated glucose concentration or immediately combined with an indicated glucose concentration to achieve a corrected glucose concentration.

Again, ordinarily, the instrument 132 will first determine the various frequency responses of the cell 31 in the various optimally uncoupling frequency ranges, with the various optimally uncoupling AC amplitudes and with the various optimally uncoupling DC offsets, followed by the determination of the indicated glucose concentration, followed by correction of the indicated glucose concentration for the thus-determined concentrations of the various interferents. However, and as previously noted, it may be desirable under certain circumstances and with certain interferents to have the instrument 132 first determine the indicated concentration of glucose before the concentrations of these interferents are determined.

Figure 4:
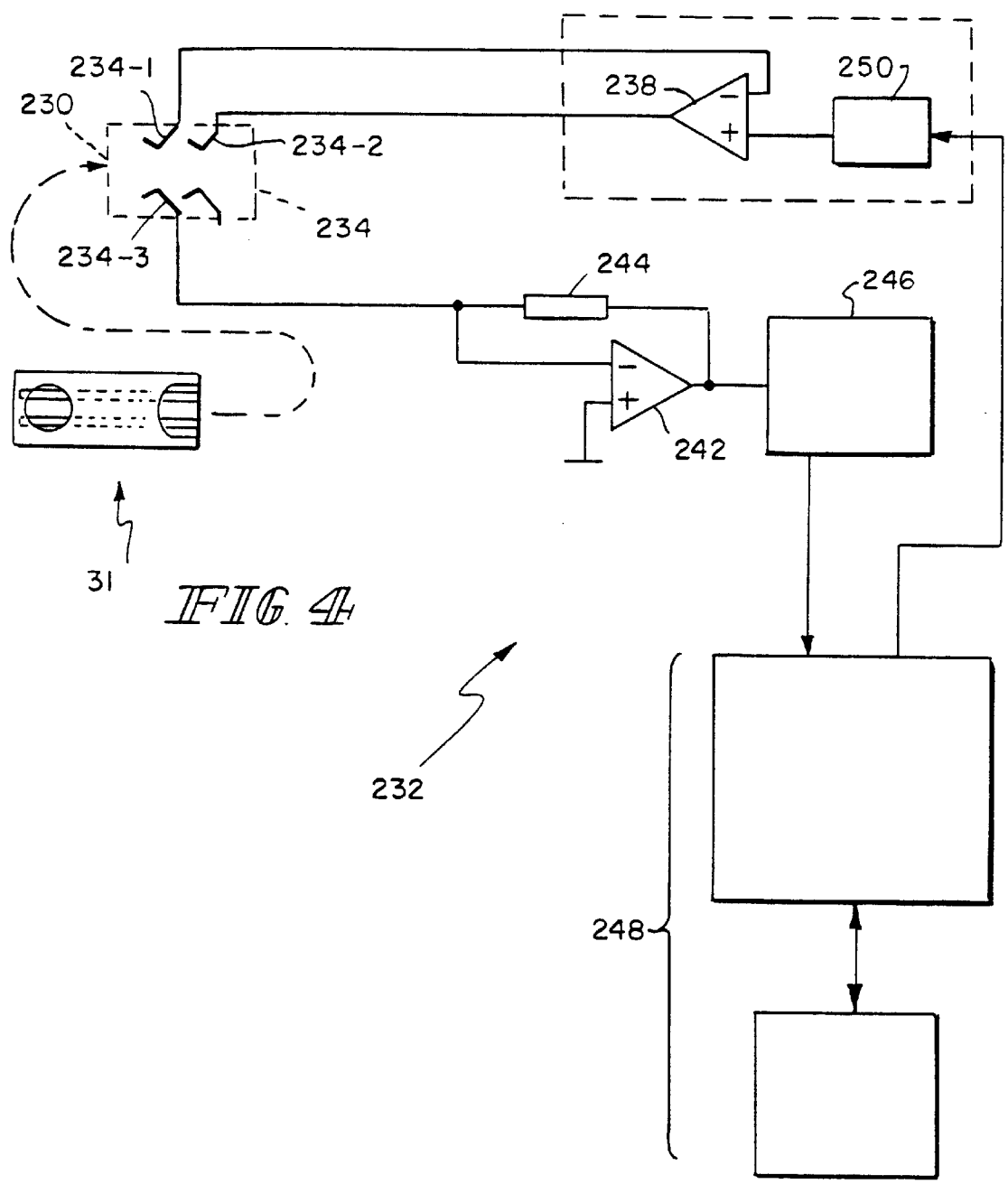
FIG. 4 illustrates a partly block and partly schematic diagram of another instrument constructed according to the present invention.

Another embodiment of the invention is illustrated in partly block and partly schematic form in FIG. 4. There, an instrument 232 includes a strip connector 230 of the same general type as strip connector 30 illustrated in FIG. 2. Strip connector 230 is designed to make contact to a biosensor 31. A first terminal 234-1 of a connector 234 is coupled to the− input terminal of a difference amplifier 238. An output terminal of amplifier 238 is coupled to a terminal 234-2 of connector 234. DC excitation across the biosensor 31 is established by the output of amplifier 238. For accurate setting of DC excitation of the biosensor 31, feedback from terminal 234-1 is returned to the− input terminal of amplifier 238. Terminals 234-1 and 234-2 contact a common electrode on biosensor 31 for enhanced accuracy of excitation. A terminal 234-3 of connector 234 is coupled to a− input terminal of a difference amplifier 242. An output terminal of amplifier 242 is coupled through a 8.25 KΩ resistor 244 to the− input terminal thereof The+ input terminal of amplifier 242 is coupled to a 1.667 V reference. An output terminal of amplifier 242 is coupled to an input terminal of a fourteen bit A/D converter 246. An output port of A/D converter 246 is coupled to an input port of a processor 248 with supporting functions which performs the indicated glucose measurement functions as described in U.S. Patents: U.S. Pat. Nos. 5,243,516; 5,288,636; 5,352,351; 5,385,846; and, 5,508,171. An output port of processor 248 is coupled to an input port of a thirteen bit D/A converter 250. Amplifier 238 and D/A converter 250 illustratively are integrated into a single device. Amplifier 238 has an open circuit shutdown mode, permitting switches 36, 136 of the embodiments illustrated in FIGS. 2–3 to be eliminated and thereby simplifying the circuit somewhat. Otherwise, the circuit illustrated in FIG. 4 functions in much the same way as the circuits illustrated in FIGS. 2–3. An output terminal of D/A converter 250 is coupled to the+ input terminal of amplifier 238. The functions of components 238, 242, 246, 248 and 250 illustratively, although not by any means necessarily, are embodied in an ASIC 252. The accuracy and resolution of D/A converter 250 and A/D converter 246 enable both AC and DC strip current measurements and thus a circuit simplification.

Again, it should be understood that the physical and chemical design characteristics of a particular cell will, to a large extent, determine the electrical characteristics of that cell. Therefore, those physical and chemical design characteristics will, to at least the same extent, determine that cell's response to each interferent, to different sample types, and to different sample volumes. It is not possible to predict, for example, in what frequency range hematocrit's concentration will be optimally uncoupled from uric acid's or bilirubin's without reference to the specific physical and chemical characteristics of that cell. Some investigation will be required to determine these optimum frequency ranges. However, the investigation will be relatively routine once the physical and chemical characteristics of the cell are known.

Figure 5:
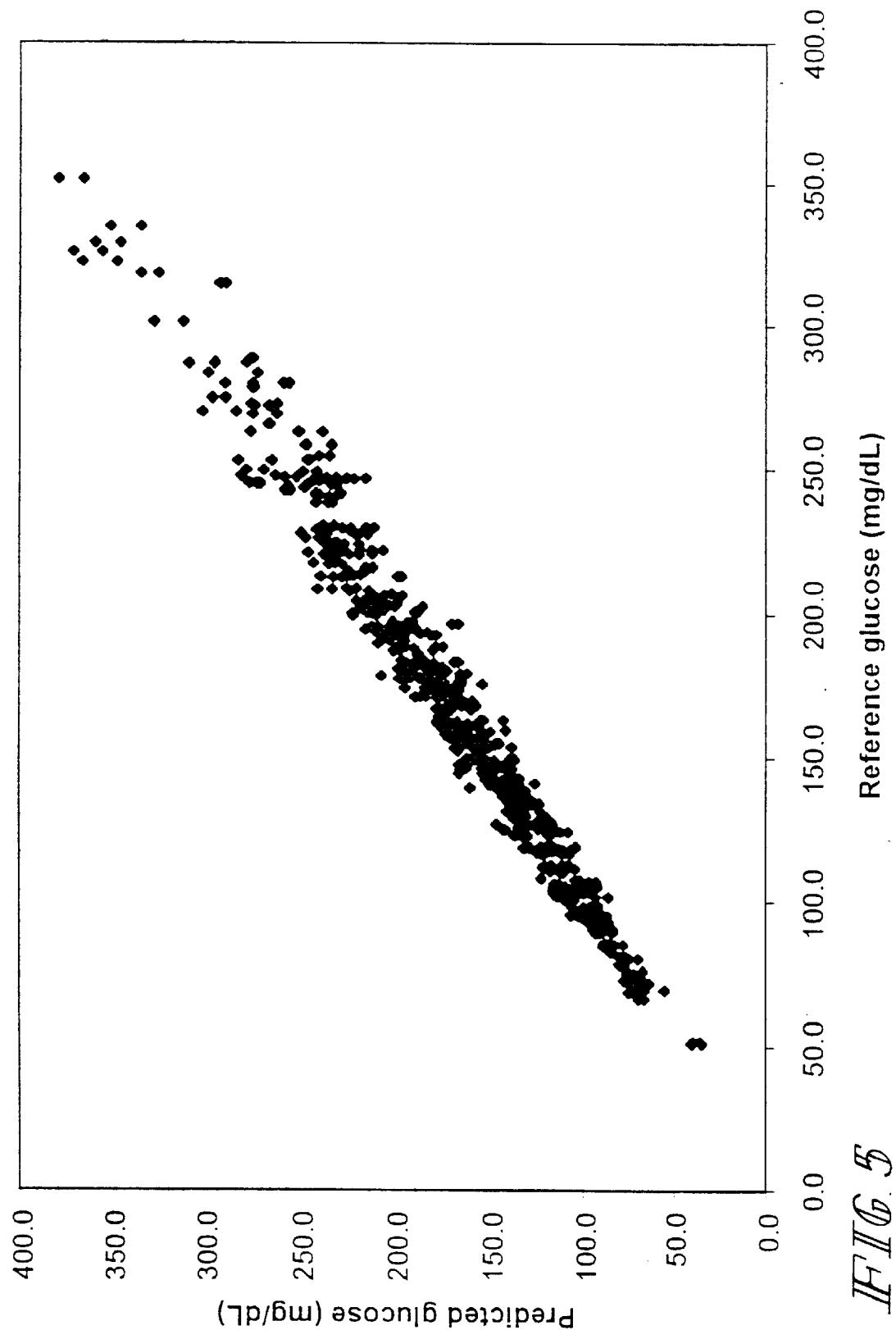
FIG. 5 illustrates glucose concentration results achieved in several forty second glucose concentration determinations with standard glucose test solutions.
Figure 9:
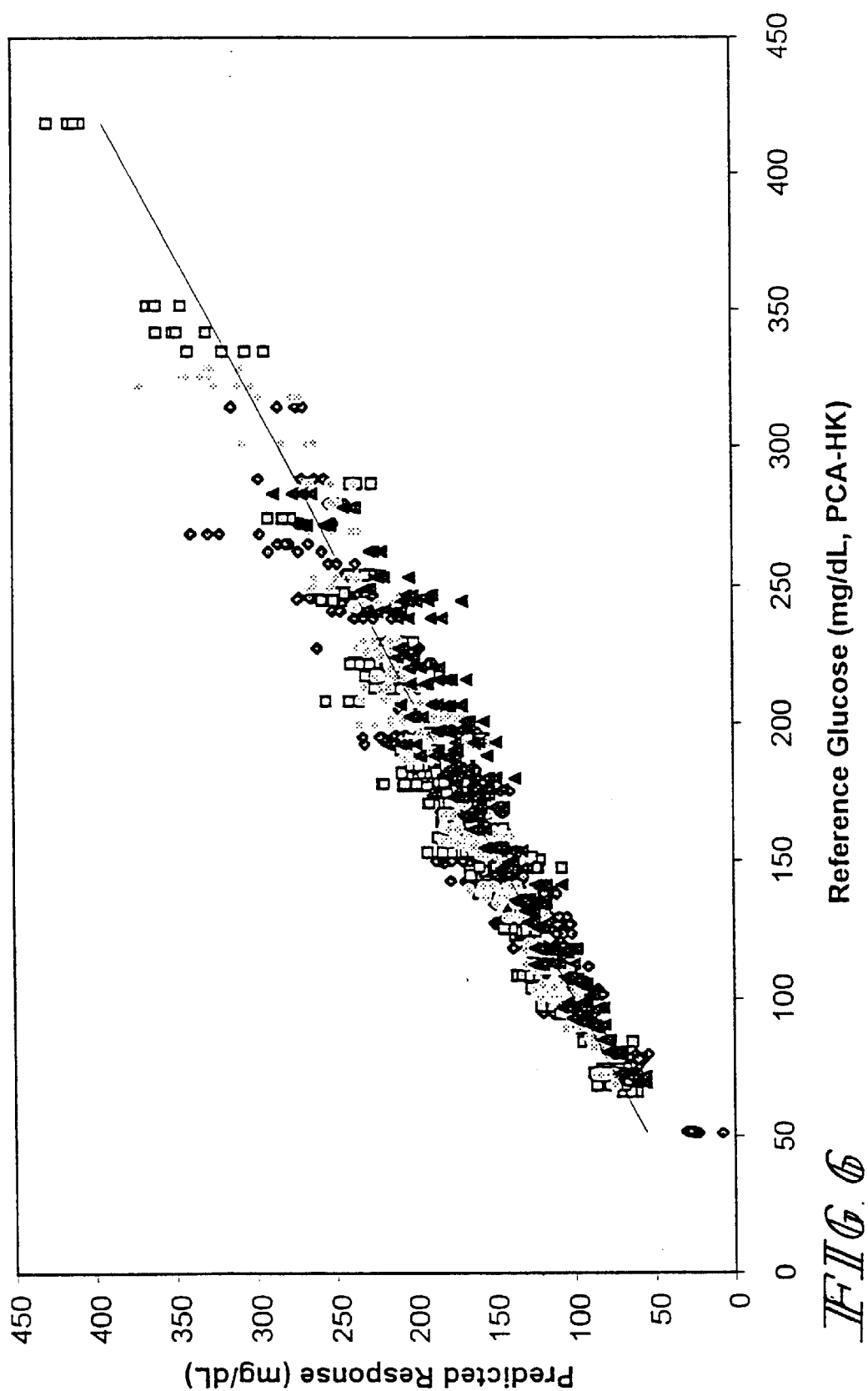
Figure 7:
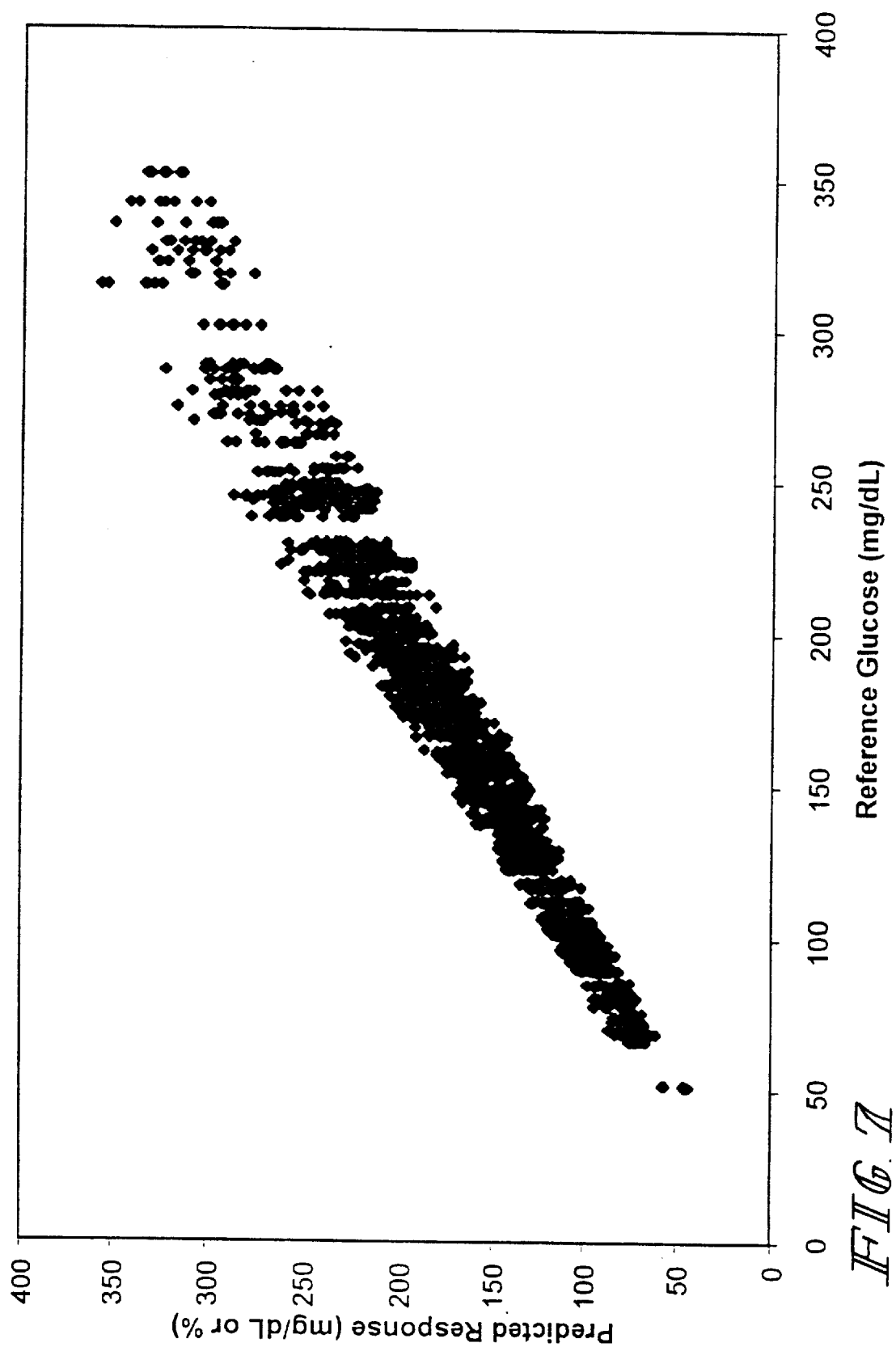

The reduction in the time required to achieve a compensated indication of the glucose concentration of blood can best be appreciated by referring to FIGS. 5–7. FIG. 5 illustrates glucose concentration results achieved in several forty second glucose concentration determinations with standard glucose test solutions. The tests whose results are illustrated in FIG. 5 were performed without impedance determination and compensation for the combined effects of temperature and hematocrit described above, but were compensated for temperature and hematocrit using prior art techniques. FIG. 6 illustrates glucose concentration results achieved in several ten second glucose concentration determinations with standard glucose test solutions. The tests whose results are illustrated in FIG. 6 were performed without impedance determination and compensation for the combined effects of temperature and hematocrit described above, but again were compensated for temperature and hematocrit using prior art techniques. FIG. 7 illustrates glucose concentration results achieved in several ten second glucose concentration determinations with standard glucose test solutions. The tests whose results are illustrated in FIG. 7 were performed using impedance determination and compensation for the combined effects of temperature and hematocrit described above. It will be appreciated from a comparison of these Figs. that the use of the impedance determination and compensation technique described above permits a reduction by a factor of four in the time required to achieve comparable glucose concentration determination in these test solutions.

What is claimed is:

1. An apparatus for determining the concentration of a medically significant component of a biological fluid, the apparatus comprising a cell for receiving a sample of the fluid, the cell supporting a chemistry which reacts with the medically significant component and first and second terminals across which the reaction of the chemistry with the medically significant component can be assessed, an instrument having first and second terminals complementary to the first and second terminals, respectively, of the cell, placement of the first and second terminals of the cell in contact with the first and second terminals, respectively, of the instrument permitting the instrument to assess the reaction, the instrument including an assessment controller configured to apply across the first and second terminals of the instrument a first signal having an AC component, to determine a first correction value in response of the cell to the first signal, to assess the reaction of the medically significant component with the chemistry and to combine the correction value with the result of the reaction assessment to produce an indication of the concentration of the medically significant component in the sample.

2. The apparatus of claim 1 wherein the assessment controller applies across the first and second terminals an AC signal.

3. The apparatus of claim 1 wherein the instrument further comprises a third terminal, placement of the first and second terminals of the cell in contact with the first and second terminals of the instrument placing one of the first and second terminals of the cell in contact with the third terminal of the instrument.

4. The apparatus of claim 3 wherein the assessment controller for determining a first correction value in response to the first signal comprises an assessment controller for feeding back a portion of the first signal appearing at the third terminal.

5. The apparatus of claim 4 wherein the assessment controller applies across a pair of the first, second and third terminals of the instrument a second signal and assesses the reaction of the medically significant component with the chemistry in response to the second signal.

6. The apparatus of claim 1 wherein the assessment controller applies across the first and second terminals of the instrument a second signal, and determines a second response to the second signal, the second response determining if the assessment controller proceeds with the application of the first signal.

7. The apparatus of claim 6 wherein the assessment controller applies across the first and second terminals an AC signal.

8. The apparatus of claim 1 wherein the instrument further comprises a third terminal, placement of the first and second terminals of the cell in contact with the first and second terminals of the instrument placing one of the first and second terminals of the cell in contact with the third terminal of the instrument.

9. The apparatus of claim 8 wherein the assessment controller feeds back a portion of the first signal appearing at the third terminal.

10. The apparatus of claim 9 wherein the assessment controller applies across a pair of the first, second and third terminals of the instrument a second signal and assesses the reaction of the medically significant component with the chemistry in response to the second signal.

11. An apparatus for determining the concentration of a medically significant component of a biological fluid, the apparatus comprising a cell for receiving a sample of the fluid, the cell supporting a chemistry which reacts with the medically significant component and first and second terminals across which the reaction of the chemistry with the medically significant component can be assessed, an instrument having first and second terminals complementary to the first and second terminals, respectively, of the cell, placement of the first and second terminals of the cell in contact with the first and second terminals, respectively, of the instrument permitting the instrument to assess the reaction, the instrument including an assessment controller configured to apply across the first and second terminals of the instrument a first signal having an AC component, determine a first response of the cell to the first signal, and determine based upon the first response whether to proceed with the determination of the concentration of the medically significant component of the biological fluid.

12. The apparatus of claim 11 wherein the assessment controller applies across the first and second terminals an AC signal.

13. The apparatus of claim 11 wherein the assessment controller applies across the first and second terminals of the instrument a second signal, determines a first correction value in response to the second signal, and combines the correction value with the result of the reaction assessment to produce an indication of the concentration of the medically significant component in the sample.

14. The apparatus of claim 13 wherein the assessment controller applies across the first and second terminals a second signal having an AC component.

15. The apparatus of claim 14 wherein the assessment controller applies across the first and second terminals an AC second signal.

16. The apparatus of claim 15 wherein the instrument further comprises a third terminal, placement of the first and second terminals of the cell in contact with the first and second terminals of the instrument placing one of the first and second terminals of the cell in contact with the third terminal of the instrument.

17. The apparatus of claim 16 wherein the assessment controller feeds back a portion of the second signal appearing at the third terminal.

18. The apparatus of claim 17 wherein the assessment controller applies across a pair of the first, second and third terminals of the instrument a third signal and assesses the reaction of the medically significant component with the chemistry in response to the second signal.

19. The apparatus of claim 13 wherein the instrument further comprises a third terminal, placement of the first and second terminals of the cell in contact with the first and second terminals of the instrument placing one of the first and second terminals of the cell in contact with the third terminal of the instrument.

20. The apparatus of claim 19 wherein the assessment controller feeds back a portion of the second signal appearing at the third terminal.

21. The apparatus of claim 20 wherein the assessment controller applies across a pair of the first, second and third terminals of the instrument a third signal and assesses the reaction of the medically significant component with the chemistry in response to the third signal.

22. A method for determining the concentration of a medically significant component of a biological fluid, the method comprising providing a cell for receiving a sample of the fluid, providing on the cell a chemistry which reacts with the medically significant component and first and second terminals across which the reaction of the chemistry with the medically significant component can be assessed, providing an instrument having first and second terminals complementary to the first and second terminals, respectively, of the cell, placement of the first and second terminals of the cell in contact with the first and second terminals, respectively, of the instrument permitting the instrument to assess the reaction, including in the instrument an assessment controller, causing the assessment controller to apply across the first and second terminals of the instrument a first signal having an AC component, causing the assessment controller to determine a first response of the cell to the first signal, and causing the assessment controller to determine based upon the first response whether to proceed with the determination of the concentration of the medically significant component of the biological fluid.

23. The method of claim 22 wherein the step of applying across the first and second terminals of the instrument a first signal comprises applying across the first and second terminals of the instrument a second signal, determining a first correction value in response to the second signal, and combining the first correction value with the result of the reaction assessment to produce an indication of the concentration of the medically significant component in the sample.

24. The method of claim 23 wherein the step of applying across the first and second terminals a second signal comprises applying across the first and second terminals an AC second signal.

25. The method of claim 24 wherein providing an instrument having first and second terminals complementary to the first and second terminals of the cell comprises providing an instrument having first, second and third terminals, placement of the first and second terminals of the cell in contact with the first, second and third terminals of the instrument permitting the instrument to assess the reaction.

26. The method of claim 25 wherein determining the second response of the cell to the second signal and converting that second response to a first correction value comprises feeding back a portion of the second signal appearing at the third terminal.

27. The method of claim 26 wherein assessing the reaction of the medically significant component with the chemistry comprises applying across a pair of the first, second and third terminals of the instrument a third signal and assessing the reaction of the medically significant component with the chemistry in response to the third signal.

28. The method of claim 22 wherein providing an instrument having first and second terminals complementary to the first and second terminals, respectively, of the cell comprises providing an instrument having first, second and third terminals, placement of the first and second terminals of the cell in contact with the first and second terminal of the instrument placing one of the first and second terminals of the cell in contact with the third terminal of the instrument.

29. The method of claim 28 wherein determining the correction value in response to the second signal comprises feeding back a portion of the second signal appearing at the third terminal.

30. The method of claim 29 wherein assessing the reaction of the medically significant component with the chemistry comprises applying across a pair of the first, second and third terminals of the instrument a third signal and assessing the reaction of the medically significant component with the chemistry in response to the third signal.

31. A method for determining the concentration of a medically significant component of a biological fluid, the method comprising providing a cell for receiving a sample of the fluid, providing the cell with a chemistry which reacts with the medically significant component and first and second terminals across which the reaction of the chemistry with the medically significant component can be assessed, providing an instrument having first and second terminals complementary to the first and second terminals, respectively, of the cell, placement of the first and second terminals of the cell in contact with the first and second terminals, respectively, of the instrument permitting the instrument to assess the reaction, providing in the instrument an assessment controller, causing the assessment controller to apply across the first and second terminals of the instrument a first signal having an AC component, determining a first correction value in response to the first signal, assessing the reaction of the medically significant component with the chemistry, and combining the correction value with the result of the reaction assessment to produce an indication of the concentration of the medically significant component in the sample.

32. The method of claim 31 wherein providing an instrument having first and second complementary terminals comprises providing an instrument having first, second and third terminals, placement of the first and second terminals of the cell in contact with the first and second terminals, respectively, of the instrument placing one of the first and second terminals of the cell in contact with the third terminal of the instrument.

33. The method of claim 32 wherein determining a first response of the cell to the first signal and converting that first response to a first correction value comprises feeding back a portion of the first signal appearing at the third terminal.

34. The method of claim 33 wherein assessing the reaction of the medically significant component with the chemistry comprises applying across a pair of the first, second and third terminals of the instrument a second signal and assessing the reaction of the medically significant component with the chemistry in response to the second signal.

35. The method of claim 34 wherein applying a second signal comprises applying a second signal having an AC component.

36. The method of claim 35 wherein applying a second signal comprises applying an AC second signal.

37. The method of claim 31 wherein applying across the first and second terminals of the instrument a first signal comprises applying across the first and second terminals of the instrument a second signal, determining a second response to the second signal, and determining if the assessment controller proceeds with the application of the first signal.

38. The method of claim 31, 32, 33, 34 or 37 wherein applying the first signal comprises applying a first AC signal.

39. An apparatus for determining the concentration of a medically significant component of a biological fluid comprising a cell for receiving a sample of the fluid, the cell supporting a chemistry which reacts with the medically significant component and first and second terminals across which the reaction of the chemistry with the medically significant component can be assessed, an instrument having first and second terminals complementary to the first and second terminals, respectively, of the cell, placement of the first and second terminals of the cell in contact with the first and second terminals, respectively, of the instrument permitting the instrument to assess the reaction, the instrument including an assessment controller configured to apply across the first and second terminals of the instrument a first signal having an AC component, determine the identity of the sample in response of the cell to the first signal, and produce an indication of the identity of the sample.

40. The apparatus of claim 39 wherein the assessment controller applies across the first and second terminals an AC signal.

41. The apparatus of claim 39 wherein the instrument further comprises a third terminal, placement of the first and second terminals of the cell in contact with the first and second terminals of the instrument placing one of the first and second terminals of the cell in contact with the third terminal of the instrument, the assessment controller applying across a pair of the first, second and third terminals of the instrument a second signal, determining a first correction value in response of the cell to the second signal, assessing the reaction of the medically significant component with the chemistry, and combining the correction value with the result of the reaction assessment to produce an indication of the concentration of the medically significant component in the sample.

42. The apparatus of claim 41 wherein the assessment controller applies across a pair of the first, second and third terminals of the instrument a third signal, and determines a third response to the third signal, the third response determining if the assessment controller proceeds with the application of at least one of the first and second signals.

43. The apparatus of claim 39 wherein the assessment controller further comprises a third terminal, placement of the first and second terminals of the cell in contact with the first and second terminals of the instrument placing one of the first and second terminals of the cell in contact with the third terminal of the instrument, the assessment controller applying across a pair of the first, second and third terminals of the instrument a second signal, determining a second response to the second signal, the second response determining if the assessment controller proceeds with the application of the first signal.

44. A method for determining the concentration of a medically significant component of a biological fluid comprising providing a cell for receiving a sample of the fluid, providing on the cell a chemistry which reacts with the medically significant component and first and second terminals across which the reaction of the chemistry with the medically significant component can be assessed, providing an instrument having first, second and third terminals, placement of the first and second terminals of the cell in contact with the first and second terminals of the instrument, providing in the instrument an assessment controller configured to apply across the first and second terminals of the instrument a first signal, determine the identity of the sample in response of the cell to the first signal, the assessment controller applying across a pair of the first, second and third terminals of the instrument a second signal, determining a first correction value in response of the cell to the second signal, assessing the reaction of the medically significant component with the chemistry, and combining the correction value with the result of the reaction assessment to produce an indication of the concentration of the medically significant component in the sample.

45. The method of claim 44 wherein the assessment controller applies across a pair of the first, second and third terminals of the instrument a third signal and determines a third response to the third signal, the third response determining if the assessment controller proceeds with the application of at least one of the first and second signals.

46. A method for determining the concentration of a medically significant component of a biological fluid comprising providing a cell for receiving a sample of the fluid, providing on the cell a chemistry which reacts with the medically significant component and first and second terminals across which the reaction of the chemistry with the medically significant component can be assessed, providing an instrument having first, second and third terminals, placement of the first and second terminals of the cell in contact with the first and second terminals of the instrument placing one of the first and second terminals of the cell in contact with the third terminal of the instrument, providing in the instrument an assessment controller configured to apply across the first and second terminals of the instrument a first signal, determine the identity of the sample in response of the cell to the first signal, and produce an indication of the identity of the sample, the assessment controller applying across a pair of the first, second and third terminals of the instrument a second signal and determining a second response to the second signal, the second response determining if the assessment controller proceeds with the application of the first signal.

* * * * *